US010400329B2

(12) United States Patent
Kerscher et al.

(10) Patent No.: US 10,400,329 B2
(45) Date of Patent: Sep. 3, 2019

(54) PROCESS FOR THE PREPARATION OF POLYCRYSTALLINE SILICON

(71) Applicant: WACKER CHEMIE AG, Munich (DE)

(72) Inventors: Michael Kerscher, Burgkirchen (DE); Reiner Pech, Neuoetting (DE); Armin Sandner, Mehring (DE)

(73) Assignee: WACKER CHEMIE AG, Munich (DE)

( * ) Notice: Subject to any disclaimer, the term of this patent is extended or adjusted under 35 U.S.C. 154(b) by 913 days.

(21) Appl. No.: 14/785,918

(22) PCT Filed: Mar. 24, 2014

(86) PCT No.: PCT/EP2014/055837
§ 371 (c)(1),
(2) Date: Oct. 21, 2015

(87) PCT Pub. No.: WO2014/173596
PCT Pub. Date: Oct. 30, 2014

(65) Prior Publication Data
US 2016/0068949 A1 Mar. 10, 2016

(30) Foreign Application Priority Data

Apr. 22, 2013 (DE) .................. 10 2013 207 251

(51) Int. Cl.
B02C 23/08 (2006.01)
C23C 16/24 (2006.01)
C01B 33/035 (2006.01)
C23C 16/01 (2006.01)
G01N 29/09 (2006.01)
C23C 16/56 (2006.01)
H01L 31/028 (2006.01)
H01L 31/0368 (2006.01)

(52) U.S. Cl.
CPC .............. C23C 16/01 (2013.01); B02C 23/08 (2013.01); C01B 33/035 (2013.01); C23C 16/24 (2013.01); C23C 16/56 (2013.01); G01N 29/09 (2013.01); H01L 31/028 (2013.01); H01L 31/03682 (2013.01); G01N 2291/0234 (2013.01)

(58) Field of Classification Search
CPC .. B02C 23/08; B02C 2015/002; C01B 33/035
USPC ............................................ 241/3, 24.1, 68
See application file for complete search history.

(56) References Cited

U.S. PATENT DOCUMENTS

| 6,309,467 | B1 | 10/2001 | Wochner et al. |
| 6,350,313 | B2 | 2/2002 | Kraus et al. |
| 8,074,905 | B2 | 12/2011 | Schaefer et al. |
| 8,216,643 | B2 * | 7/2012 | Kim ...................... C01B 33/035 427/255.11 |
| 8,747,794 | B2 | 6/2014 | Pech et al. |
| 9,006,002 | B2 * | 4/2015 | Netsu ..................... C01B 33/035 438/14 |
| 2006/0243834 | A1 | 11/2006 | Schantz et al. |
| 2007/0235574 | A1 * | 10/2007 | Schaefer ................. B02C 21/00 241/36 |
| 2008/0053232 | A1 | 3/2008 | Hegen et al. |
| 2008/0286550 | A1 * | 11/2008 | Sofin ..................... C01B 33/035 428/220 |
| 2009/0081108 | A1 | 3/2009 | Sakai et al. |
| 2009/0081380 | A1 | 3/2009 | Endoh et al. |
| 2009/0120848 | A1 | 5/2009 | Schaefer et al. |
| 2010/0219380 | A1 | 9/2010 | Hertlein et al. |
| 2012/0111263 | A1 * | 5/2012 | Bonauer-Klepp .... C01B 33/037 117/38 |
| 2012/0175613 | A1 * | 7/2012 | Netsu ..................... C01B 33/035 257/49 |
| 2013/0102092 | A1 | 4/2013 | Netsu et al. |
| 2013/0186325 | A1 | 7/2013 | Wochner et al. |

FOREIGN PATENT DOCUMENTS

| EP | 2 036 856 A2 | 3/2009 |
| EP | 2 479 142 A1 | 7/2012 |
| JP | H1015422 A | 1/1998 |
| JP | 2006-206387 A | 8/2006 |

* cited by examiner

Primary Examiner — Elaine Gort
Assistant Examiner — Christopher B Wehrly
(74) Attorney, Agent, or Firm — Brooks Kushman P.C.

(57) ABSTRACT

Siemens reactors for polysilicon deposition may employ faster and/or more economical deposition conditions without reduction in yield, by pre-sorting polysilicon rods into different quality classifications prior to comminution, and further sorting the polysilicon fragments in each classification into further classifications.

17 Claims, No Drawings

PROCESS FOR THE PREPARATION OF POLYCRYSTALLINE SILICON

CROSS REFERENCE TO RELATED APPLICATIONS

This application is the U.S. National Phase of PCT Appln. No. PCT/EP2014/055837 filed Mar. 24, 2014, which claims priority to German Application No. 10 2013 207 251.1 filed Apr. 22, 2013, the disclosures of which are incorporated in their entirety by reference herein.

BACKGROUND OF THE INVENTION

1. Field of the Invention

The invention relates to a process for production of polycrystalline silicon.

2. Description of the Related Art

Polycrystalline silicon (polysilicon for short) serves as a starting material for production of monocrystalline silicon for semiconductors by the Czochralski (CZ) or zone melting (FZ) process, and for production of mono- or polycrystalline silicon by various pulling and casting processes for production of solar cells for photovoltaics.

Polycrystalline silicon is generally produced by means of the Siemens process. In this process, in a bell jar-shaped reactor ("Siemens reactor"), support bodies, typically thin filament rods of silicon, are heated by direct passage of current and a reaction gas comprising hydrogen and one or more silicon-containing components is introduced.

Typically, the silicon-containing component used is trichlorosilane ($SiHCl_3$, TCS) or a mixture of trichlorosilane with dichlorosilane ($SiH_2Cl_2$, DCS) and/or with tetrachlorosilane ($SiCl_4$, STC). Less commonly, but on the industrial scale too, silane ($SiH_4$) is used.

The filament rods are inserted perpendicularly into electrodes at the reactor base, through which they are connected to the power supply.

High-purity polysilicon is deposited on the heated filament rods and the horizontal bridge, as a result of which the diameter thereof grows with time.

After the rods have cooled down, the reactor bell jar is opened and the rods are removed by hand or with the aid of specific apparatus, called deinstallation aids, for further processing or for temporary storage.

Both the storage and the further processing, in particular comminution of the rods, classification and packing of broken pieces, are generally effected under special environmental conditions in climate-controlled rooms, which prevents contamination of the product.

Between the time of opening of the reactor and storage or further processing, the material deposited, however, is exposed to environmental influences, especially dust particles.

The morphology and microstructure of the growing rod are determined by the parameters of the deposition process. The morphology of the deposited rods may vary from compact and smooth (as described, for example, in U.S. Pat. No. 6,350,313 B2) to very porous and fissured material (as described, for example, in US2010/219380 A1).

In the production of thick polycrystalline silicon rods (diameter>100 mm) in the Siemens reactors according the prior art, a relatively frequent observation is that the rods have regions with a very rough surface ("popcorn"). These rough regions have to be separated from the rest of the material, typically by visual checking after crushing, and are sold at much lower prices than the rest of the silicon rod.

Increasing the base parameters in the course of deposition (temperature of the rods, specific flow rate, concentration) generally leads to an increase in the deposition rate and hence to an improvement in the economic viability of the deposition process.

However, each of these parameters is subject to natural limits, exceedance of which disrupts the production process (according to the configuration of the reactor used, the limits are somewhat different).

If, for example, the chosen concentration of the silicon-containing component is too high, there may be homogeneous gas phase deposition.

The result of an excessively high rod temperature may be that the morphology of the silicon rods to be deposited is not compact enough to provide a sufficient cross-sectional area for the current flow as it rises with growing rod diameter. Excessively high current density can cause the melting of silicon.

In the case of rods of high diameter (120 mm and above), the choice of temperature is even more critical, since silicon within the rod can become liquid (because of the high temperature differences between the surface and the rod center), even when the morphology is compact.

Demands on the product from customers in the semiconductor and solar industries also distinctly restrict the ranges for the process parameters.

For example, FZ applications require silicon rods which are very substantially free of cracks, pores, discontinuities, fissures, etc. and hence are homogeneous, dense and solid. Moreover, for a better yield in FZ pulling, they should preferably have a particular microstructure. A material of this kind and the process for production thereof are described, for example, in US2008/286550 A1.

For the production of recharge rods and what are called cut rods, which are used principally in the CZ process to increase the crucible fill level, crack-free and low-stress raw polycrystalline silicon rods are likewise required.

For most applications, however, polycrystalline silicon rods are crushed to small pieces which are typically then classified by size. A process and an apparatus for comminution and sorting of polysilicon is described, for example, in US 2007/235574 A1.

US 2009081108 A1 discloses a workbench for manual sorting of polycrystalline silicon by size and quality. This involves implementation of an ionization system in order to neutralize electrostatic charges resulting from active air ionization. Ionizers permeate the cleanroom air with ions such that static charges at insulators and ungrounded conductors are dissipated.

US 2007235574 A1 discloses a device for comminuting and sorting polycrystalline silicon, comprising a feed for a coarse polysilicon fraction into a crushing system, the crushing system and a sorting system for classifying the polysilicon fraction, wherein the device is provided with a controller which allows variable adjustment of at least one crushing parameter in the crushing system and/or at least one sorting parameter in the sorting system. A polysilicon rod is placed on the crushing table of the pre-comminuter. Visual quality control of the rod for foreign bodies, deposits and morphology of the surface is carried out on the crushing table. The rod is placed on a crushing carriage, which conveys the rod automatically into the crushing chamber.

In the processing to chunks, rods with cracks and other material defects are accepted as starting material. However, the morphology of polycrystalline rods and chunks formed therefrom has a strong influence on the performance of the product. Typically, a porous and fissured morphology has an adverse effect on the crystallization characteristics.

This particularly affects the demanding CZ process, in which porous and fissured chunks were not usable because of the economically unacceptable yields.

Other crystallization processes (for example block casting, which is the most frequently used method for production of solar cells) are less morphology-sensitive. Here, the adverse effect of the porous and fissured material can be compensated for in economic terms by its lower production costs.

It is a problem that, in the production of compact materials, porous fractions sometimes also arise in the region of the top ends of the rods. In the case of demanding customer applications, however, porous rod fractions are unwanted, and so the reactor running curves have to be planned more "conservatively" than actually necessary, in order to avoid the last porous fractions as well.

On the other hand, the production of porous silicon also gives rise to compact fractions in the lower parts of the rods and on the rod edges facing the reactor wall.

In some cases, particular parts of rods are more heavily contaminated with impurities than others. EP 2479142 A1 discloses a process for producing a polycrystalline silicon chunk, comprising deposition of polycrystalline silicon on a support body in a reactor, withdrawing the polycrystalline silicon rod from the reactor and comminuting the silicon rod into silicon chunks, with removal of at least 70 mm from the electrode end of the polycrystalline silicon rod prior to the comminution. Here, part of the rod is thus removed before the comminution of the rod into chunks. The chunks obtained by comminution of the residual rod have a low content of chromium, iron, nickel, copper and cobalt.

These problems gave rise to the objectives of the invention.

SUMMARY OF THE INVENTION

The invention is directed to a process for producing polycrystalline silicon, comprising depositing polycrystalline silicon on support bodies present in at least one reactor to obtain polycrystalline silicon rods, deinstalling the polycrystalline silicon rods from the at least one reactor, and comminuting the deinstalled polycrystalline silicon rods into chunks, wherein the deinstallation of the polycrystalline silicon rods from the at least one reactor is followed by, and the comminution of the deinstalled polycrystalline silicon rods into chunks is preceded by, classification of the polycrystalline silicon in rod form into at least two quality classes on the basis of at least one feature, said at least two quality classes being sent to separate further processing steps.

DETAILED DESCRIPTION OF THE PREFERRED EMBODIMENTS

The invention thus envisages undertaking a classification of the deinstalled silicon rods into at least two quality classes. This classification precedes the comminution of the rods into chunks.

In the context of the invention, comminution into chunks is understood to mean the comminution step immediately prior to the packing of the polycrystalline silicon or a cleaning step which precedes the packing.

Comminution into chunks gives rise to chunk sizes which can be assigned to the following size classes, each of which is defined as the longest distance between two points on the surface of a silicon chunk (=max. length):
  Chunk size 0 [mm] 1 to 5;
  Chunk size 1 [mm] 4 to 15;
  Chunk size 2 [mm] 10 to 40;
  Chunk size 3 [mm] 20 to 60;
  Chunk size 4 [mm] 45 to 120;
  Chunk size 5 [mm] 90 to 200
  Chunk size 6 [mm] 130 to 400

Crushing of the polycrystalline silicon rods into rod pieces or removing a surface of a polycrystalline silicon rod or taking a sample from the silicon rod for analysis purposes, especially for analysis with respect to a classification feature, is not to be understood as comminution of the polycrystalline silicon rod in the context of the invention.

The classification into at least two quality classes can be effected using the polycrystalline silicon rods taken from only one reactor. However, it is also preferable to consider a plurality of reactors and to classify the polycrystalline silicon rods from these reactors.

Preferably, the at least two different further processing steps lead to at least two different product classes of the polycrystalline silicon, for example from the three umbrella classes
  use for semiconductor applications;
  use for mono(crystalline) solar;
  use for multi(crystalline) solar.

It is also possible to view different chunk sizes as different product classes; for example, a further processing step can be "comminution to chunk size 5", and another, different further processing step can be "comminution to chunk size 3".

The effect of the classification may be that whole rods are assigned to particular quality classes.

The effect may also be to assign divided parts of rods to particular quality classes.

It is likewise possible for a silicon-filled transport means to be assigned to a particular quality class on the basis of a sample taken from the transport means.

The classification features cited hereinafter are preferably employed individually or in any possible combinations.

The classification feature may be the feature "position of the silicon in the rod".

The classification feature may be the feature "position of the rod in the reactor".

The classification feature may be a visually discernible feature.

The classification feature may be a measurable feature.

The measurable feature may be a mechanically measurable feature selected from the group consisting of hardness of the rods or rod parts, flexural strength of the rods or rod parts, tensile strength of the rods or rod parts, compressive strength of the rods or rod parts, shear strength of the rods or rod parts, sound of the rods or rod parts after mechanical excitation, intrinsic vibration frequency of the rods or rod parts, fracture characteristics of the rods or rod parts, spontaneously or on fragmentation by various methods (mechanically, thermally, electrically), stresses within the rods or rod parts and moment of inertia of the rods or rod parts, and combinations of the features mentioned.

This measurable feature may likewise be a feature measurable by electromagnetic/nuclear means, selected from the group consisting of thermal conductivity of the rods or rod parts, electrical resistance of the rods or rod parts, electromagnetic permeability of the rods or rod parts, refractive indices of the rods or rod parts for electromagnetic waves, refractive indices of the rods or rod parts for sound, infrasound and ultrasound waves, color of the rods or rod parts, absorption spectrum of the rods or rod parts, emission spectrum of the rods or rod parts after excitation (for example thermally, electrically, optically) or in the unexcited state, X-ray diffraction characteristics of the rods or rod parts, X-ray absorption characteristics of the rods or rod parts, neutron diffraction characteristics of the rods or rod parts, neutron absorption characteristics of the rods or rod parts, nuclear spin resonance characteristics of the rods or rod parts, electrical capacitance of the rods or rod parts, electromagnetic inductivity of the rods or rod parts, magnetization of the rods or rod parts, magnetic moment of the rods or rod parts, magnetic susceptibility of the rods or rod parts, radioactivity of the rods or rod parts, isotope composition of the rods or rod parts, neutron activatability of the rods or rod parts, gloss of the rods or rod parts, reflectivity of the surface of the rods or rod parts for various wavelengths of electromagnetic radiation, reflectivity of fracture surfaces of the rods or rod parts for various wavelengths of electromagnetic radiation, heat transfer coefficient of the surface or fracture surface of the rods or rod parts, impedance of the rods or rod parts for electromagnetic or sound waves of different frequencies and electrical polarizability of the rods or rod parts and electrical permittivity of the rods or rod parts and combinations of the features mentioned.

The measurable feature may additionally be selected from the group consisting of stains on the surface of the rods or rod parts, surface deformations of the rods or rod parts, surface structure of the rods or rod parts, thickness of the rods or rod parts, shape of the rods or rod parts, length of the rods, weight of the rods or rod parts, porosity of the rods or rod parts, density of the rods or rod parts and appearance of the rods or rod parts (personal visual quality impression) and combinations of the features mentioned.

The classification feature may, for example, be the rod diameter.

The classification feature may be the feature "contamination of the surface or of the volume".

In this case, it is possible to classify by surface contamination of the rods or rod parts with metals, nonmetals or compositions, by contamination of the volume of the rods or rod parts with metals, nonmetals or compositions, and by contamination of the surface of the rods or rod parts with dust (e.g. silicon dust), or by a combination of the features mentioned.

Further preferred classification features are air temperature and composition (including contaminants) on rod deinstallation and in the time up to classification, state of the deposition reactor after deposition (integrity, deposits of various substances), any contact of the rods or rod parts with extraneous materials.

Suitable classification features are also the crystal structure of the rods or rod parts, the crystallite size, type, shape and arrangement in regions within or on the surface of rods or rod parts, the interface of the filament rods with the deposited silicon (color, shape, thickness and composition of any existing intermediate layer, bond strength etc.) and the presence or absence of (for example gas-filled) cavities within the rods or rod parts, and combinations of the features mentioned.

Finally, it is also possible to classify by the reaction characteristics of the rods or rod parts with various chemicals, the odor of the rods or rod parts and the particle emission of the rods or rod parts.

The invention preferably also envisages separation of a portion of a silicon rod in order to classify this portion on the basis of a classification feature, for example by removing the surface or crushing the rod into large chunks.

More preferably, the comminution into chunks is additionally followed by a classification of the chunks on the basis of at least one classification feature selected from the group consisting of porosity, cracks, holes, stains, and rod diameter and shape.

It is also preferable to classify before and during the deposition. As already mentioned before, it is preferable to consider a plurality of reactors and to classify the polycrystalline silicon rods from these reactors.

Suitable classification features prior to the deposition are reaction gases (contamination by metals, nonmetals and extraneous gases) and the filament rods used (thickness, shape, length, and contamination on the surface and in the volume).

During the deposition, a useful classification feature is one selected from the group consisting of chosen reactor type, chosen configuration of the reactor (electrodes, nozzles, seals etc.), deposition temperature and the profile thereof during the deposition, flow rate of the reaction gases and the profile thereof during the deposition, composition and concentration of the reaction gases and the profile thereof during the deposition and deposition time. It is also preferable to combine two or more classification features from the group mentioned.

In a preferred embodiment, classification is effected by the position in the rod.

This is done, for example, when substantially compact material, as required for demanding customer processes, is deposited in the Siemens reactor. As mentioned above, porous fractions also occur at particular rod positions. Especially the top ends of the rods are often highly porous. The intention is to classify the rod positions into compact and porous. In this way, the rod positions are assigned to the two quality classes of compact and porous. The porous rod parts are removed, so resulting in rod parts which include only compact fractions and rod parts which also include porous fractions. The rod parts which also include porous fractions are processed further by comminution into chunks for the solar industry (solar product class). The compact rod parts are assigned to the semiconductor product class (FZ, CZ). The compact rod parts are optionally comminuted into chunks.

The advantages of this embodiment arise from the fact that porous fractions in the deposition can now no longer influence the performance of the crystallization process since they have been separated beforehand. On the other hand, the porous rod parts are assigned only to the solar product class and processed further therein. In this case, the porous parts do not just meet the demands for solar silicon but actually lead to an improvement in performance. This enables faster and hence less expensive deposition in the production of compact material.

In a further preferred embodiment, classification is effected by position in the reactor.

This is based on the consideration of selecting rods by their position in the reactor during the deposition.

The arrangement of the rods in the reactor influences the quality of the rods deposited. Modern reactors encompass at least 20 filament rods which serve as support bodies for deposition of polycrystalline silicon. A reactor also provides gas inlet orifices for reaction gas in the reactor chamber, which are nozzles aligned vertically upward with respect to a base plate of the reactor chamber. A nozzle may also be provided in the center of the base plate. One or more offgas orifices are preferably positioned in the middle of the reactor around the central nozzles or alongside the central nozzles and/or between reactor wall and the outer silicon rods.

Preferably, the reactor chamber has a round cross section or one adapted to the number of filament rods and optimal utilization of space, for example a hexagonal cross section.

In this context, it is advantageous when each silicon rod (excluding rods alongside the reactor wall) has, at a distance of 150 to 450 mm, three further silicon rods and one to three input gas nozzles. Said three further silicon rods are referred to as adjacent rods or neighboring rods. Preferably, the distance from nozzles and neighboring rods is between 200 and 350 mm. The individual distances between the adjacent silicon rods or nozzles may differ, but are preferably between 150 and 450 mm, more preferably between 200 and 350 mm. Any difference in the distances from the individual adjacent silicon rods and nozzles is preferably less than 50%, more preferably less than 25% and most preferably at less than 10%. The silicon rods alongside the reactor wall have, at the same distance, only 1 to 3 further silicon rods and 1 to 3 gas inlet orifices. The angles between the directions from silicon rod to the neighboring rods and from the silicon rod to the neighboring nozzles are preferably between 90 and 150°, more preferably between 105 and 135°, most preferably 115-125°.

If polycrystalline silicon rods are produced in reactors having such a rod arrangement, these have a significantly lower popcorn level.

For the same rod quality, it is possible to run much faster and hence much more economic deposition processes (for example because of higher temperature of the silicon rods).

In principle, it is possible for rods in the middle of the reactor to attain higher temperatures and hence to grow more quickly and with higher porosity than the rods on the outside, close to the reactor wall.

Through selection of the rods, it was possible to deposit material for two different quality classes within a reactor charge, namely almost completely compact material suitable for semiconductor processes after cleaning, and inexpensive porous silicon as utilized for solar processes. The total costs here were lower than in the case of separate production of the two materials.

In a further preferred embodiment, classification is effected according to morphology.

In particular cases, it is impossible to predict the morphology and hence the suitability of the material for particular customer processes from the position of the silicon in the rod or of the rod in the reactor.

In these cases, deinstallation of the rods may be followed directly by a classification on the basis of the morphology of the rods (holes, cracks etc.): in this case, either whole rods or else parts of these rods (for example including peeled surfaces) are classified into particular quality classes.

One example of a possible method for this purpose is a method for the noncontaminating and nondestructive testing of a shaped polysilicon body for a material defect, in which ultrasound waves pass through the shaped polysilicon body, with ultrasound coupling by means of bubble-free demineralized water in a water-jet technique, and with registration of the ultrasound waves by an ultrasound receiver after they have passed through the shaped polysilicon body, such that defects in the polysilicon material are detected. Details of this method can be found in US 20080053232 A1. By means of the method, it is possible to sort by defects having a projection area greater than 0.03 mm². A possible classification feature is the presence or absence of defects of this size. Accordingly, sorting into two quality classes is accomplished. The shaped polysilicon body examined may be a polycrystalline silicon rod or a separated part of a rod.

The quality class with defects is sent to a different further processing operation and hence optionally to a different product class than the other quality class.

As well as the classification features mentioned, it is also possible to classify by further conspicuous features. Further conspicuous features may, for example, be deposits or stains, which can also occur only on a single rod in a batch. If the conspicuous feature occurs only on one rod, only this rod is optionally excluded. The rest of the batch is sent to the planned use. The excluded rod is assigned to another, lower quality class.

It is also preferable to undertake such classifications by morphological features and by other conspicuous features after the comminution of silicon rods, i.e. on the chunks.

In this case, the chunks are classified on the basis of at least one feature into at least two quality classes, in which case said at least two quality classes are sent to at least two different further processing steps, in which case said at least two different processing steps lead to two different product classes.

This classification of chunks may also follow a wet-chemical treatment. Specifically after a wet chemical treatment, stains often occur on individual chunks. A suitable wet-chemical treatment is described in EP 0 905 796 B1.

It is especially preferable to provide workers on the cleaning line with a catalog of stains showing stains that typically occur on chunks. This can be used by the worker to undertake a classification of the chunks.

It is likewise advantageous when the worker is also provided with a use matrix that gives him or her information, on the basis of the classification according to the stain catalog, as to the use to which the conspicuous chunk is to be sent.

These measures, such as provision of a catalog of stains or generally of features and of a use matrix, are advantageous for all classifications based on visual assessment by an individual.

In all embodiments, the classification of the polycrystalline silicon rods may precede or follow the removal of the carbon electrode. The removal of the carbon electrode and of carbon-contaminated Si chunks is not considered to be a classification step in the context of this invention.

A further classification feature is the dopant content. In this case, the measurement can be effected at various points on a rod by taking a sample.

For this purpose, small samples which have been produced from a polycrystalline silicon rod (for example by drilling) are introduced into a silicon vessel and processed with the silicon vessel to give a single crystal. Here, however, it is necessary to subtract the concentrations in the bulk and the contamination of the silicon vessel from the total contaminant determined.

In that case, dopants (B, P, As, Al) are analyzed to SEMI MF 1398 on an FZ single crystal produced from the polycrystalline material (SEMI MF 1723) by means of photoluminescence.

A wafer is divided from the monocrystalline rod produced from a polycrystalline silicon rod or from polycrystalline silicon chunks by means of FZ, etched with $HF/HNO_3$, rinsed with 18 MOHm water and dried. The photoluminescence measurements are conducted on this wafer.

The at least two different further processing steps may involve, for example, sending one quality class having an excessively high dopant content at the surface to a wet-chemical treatment, while the other quality class is processed further without such a cleaning step.

With regard to the at least two product classes, a first distinction should be made between semiconductor and solar.

In the case of semiconductor, a further differentiation is made between FZ (product: rod) or CZ chunks, which may or may not have been cleaned.

In the case of solar, a differentiation is made according to the nature of the deposition process.

One product class provides a polycrystalline silicon rod having a diameter of at least 150 mm, including a core (A) having a porosity of 0 to less than 0.01 and a thin rod (support body, filament) and at least two successive regions B and C having porosity differing by a factor of 1.7 to 23, the outer region C being less porous than the region B.

A region of the silicon rod having a porosity of less than 0.01 is regarded as compact in the context of the invention. The core of the silicon rod is thus compact in this product class. A region having a porosity of 0.01 to 0.1 is referred to as "dense material" or "dense layer". Region C comprises dense material.

Preferably, core A extends over a diameter range of up to 60 mm. The thin rod on which the core A has been deposited typically has an extent of a few mm up to 12 mm. Thus, core A typically starts, for example, at a diameter of 9 mm and extends up to a diameter of not more than 60 mm. Core A preferably extends up to a diameter of not more than 50 mm, more preferably not more than 40 mm.

Preferably, the region B which follows the core A has the greatest porosity of 0.06 to 0.23 and extends over a diameter range of 15% to 90% of the diameter of the silicon rod. Preferably, region B extends over a diameter range of 20-80%.

Preferably, the region C which follows has a lower porosity of 0.01 to 0.1 and extends over a diameter range of 50% to 100% of the total diameter of the silicon rod. Region C preferably extends over a diameter range of 60-100%, more preferably over a range of 70-100%.

Preferably, the porosity in the region C is constant. It is more preferable when the porosity in region C decreases with increasing diameter.

It is additionally preferable when a final layer Z has been applied to the porous regions B and C, the porosity of Z being 0 to less than 0.01 (compact) in a diameter range of 90% to 100% of the total diameter. A particularly preferred diameter range is 95-100%.

Preferably, the Z layer has a thickness of at least 7.5 mm.

By comminution of such a polycrystalline silicon rod, it is possible to produce polycrystalline silicon chunks.

The comminution of the rods is preferably effected analogously to EP 2 423 163 A1 with subsequent removal of dust from the chunks by means of compressed air or dry ice. It is likewise preferable, analogously to U.S. Pat. No. 8,074,905, to crush the rods into chunks, to classify or sort them into chunks of size classes from about 0.5 mm to 200 mm, and then to subject them to a wet-chemical cleaning operation—as described in EP 0 905 796 B1.

It is a feature of the polycrystalline silicon chunks obtained that they include chunks having different porosities and/or chunks comprising regions having different porosities.

Thus, the chunks can also be classified by porosity.

The porosities of individual chunks vary from 0 to 0.25.
The result is two quality classes:

Individual chunks have a porosity of 0 to less than 0.01 and originate from the compact core of the silicon rod or from the Z layer optionally present.

Other chunks have varying degrees of porosity and have porosities of 0.01 to 0.25.

The overall porosity of a sample is composed of the sum total of the cavities connected to one another and to the environment, and the cavities not connected to one another. The overall porosity, i.e. the proportion of the total pore volume (open and closed pores) in the total volume of the polysilicon, is determined to DIN-EN 1936 from the calculation of apparent density and real density, i.e.

$$\text{total porosity} = 1 - (\text{apparent density}/2.329 \ [\text{g/cm}^3]).$$

The apparent density is defined as the density of the polysilicon including the pore space in the dry state to DIN-EN 1936 (weighing of specimens defined in terms of volume or measurement of the buoyancy force of the saturated sample in mercury with a hydrostatic balance).

The compact core A of the polycrystalline silicon rod preferably has a apparent density of 2.329 (porosity 0). Region B preferably has a apparent density of 1.8 to 2.2. Region C preferably has a apparent density of 2.1 to 2.3. Layer Z preferably has a apparent density of 2.25 to 2.329.

A further product class provides a polycrystalline silicon rod comprising an outer layer of polycrystalline silicon having a thickness of 0.01 to 20 mm, this outer layer including crystallites having a mean size of more than 20 µm.

Preferably, the mean size of the crystallites of the outer layer is not more than 80 µm. Preferably, the mean size of the crystallites of the outer layer is 25-60 µm, more preferably 30-60 µm, most preferably 35-55 µm.

Preferably, the polycrystalline silicon rod has a porous or fissured structure below the outer layer.

Preferably, the structure in the interior of the polycrystalline silicon rod is of the same type (i.e. has the same crystal structure, crystallite size etc. in the interior), and comprises pores, discontinuity gaps, cracks and fissures.

Preferably, the outer layer consists of crystallites having a mean size greater than the mean size of the crystallites beneath the outer layer.

The invention thus enables classification by compact and porous fractions of the polycrystalline silicon. The deposition processes which constitute a significant cost block in polysilicon production can be run much more flexibly. High-quality material is also sent to a high-quality use. Compact material formed in the production of solar products can also be used for higher-quality products (CZ).

The invention claimed is:

1. A process for producing comminuted polycrystalline silicon, comprising depositing polycrystalline silicon on support bodies present in at least one reactor to obtain polycrystalline silicon rods, deinstalling the polycrystalline silicon rods from the at least one reactor, and comminuting the deinstalled polycrystalline silicon rods into chunks, wherein the deinstallation of the polycrystalline silicon rods from the at least one reactor is followed by, and the comminution of the deinstalled polycrystalline silicon rods into chunks is preceded by, classification of whole polycrystalline silicon rods or rod form parts separated therefrom into at least two quality classes of polycrystalline silicon on the basis of at least one classification feature, said at least two quality classes being sent to separate further processing steps.

2. The process of claim 1, wherein the at least one classification feature of the polycrystalline silicon rods or rod form parts is the position of the silicon in the rod or rod form part being classified.

3. The process of claim 1, wherein the at least one classification feature of the polycrystalline silicon rods or rod form parts is the position in the reactor of the rod or rod form part being classified.

4. The process of claim 1, wherein the at least one classification feature of the polycrystalline silicon rods or rod form parts is a visually discernible feature on the rod or rod form part being classified.

5. The process of claim 1, wherein the at least one classification feature of the polycrystalline silicon rods or rod form parts is a measurable feature of the rod or rod form part being classified.

6. The process of claim 5, wherein the at least one classification feature of the polycrystalline silicon rods or rod form parts is the rod diameter of the rod or rod form part being classified.

7. The process of claim 1, wherein the at least one classification feature of the polycrystalline silicon rods or rod form parts is contamination of the surface or of the volume of the rod or rod form part being classified.

8. The process of claim 1, wherein the polycrystalline silicon rods classified into at least two quality classes include whole polycrystalline silicon rods.

9. The process of claim 1, wherein rod form parts from a whole polycrystalline silicon rod of the deinstalled polysilicon rods are assigned to at least two quality classes.

10. The process of claim 1, wherein the comminution of the polycrystalline silicon rods or rod form parts into chunks is followed by a classification of the chunks into at least two quality classes on the basis of at least one feature selected from the group consisting of porosity, cracks, holes, stains, rod diameter and rod shape.

11. The process of claim 1, wherein following said separate further processing steps, at least two product classes including at least two of three classes a) through c):
 a) polycrystalline silicon for monocrystalline solar applications,
 b) polycrystalline silicon for multicrystalline solar application, and
 c) polycrystalline silicon for semiconductor applications, are collected.

12. The process of claim 1, wherein the support bodies are filament rods consisting essentially of silicon.

13. The process of claim 11, wherein one product class collected is polycrystalline silicon for semiconductor applications, and this class is comprised of dense cores of the polycrystalline silicon rods.

14. The process of claim 1, wherein at least one quality class is a dense first polycrystalline silicon quality class, and a further second quality class is of polycrystalline silicon with a density less than the density of the polycrystalline silicon of the first quality class.

15. The process of claim 1, wherein the classification into quality classes is based on one or more features selected from the group consisting of porosity, cracks, holes, stains and rod shape.

16. A process for producing polycrystalline silicon, comprising depositing polycrystalline silicon on support bodies present in at least one reactor to obtain polycrystalline silicon rods, deinstalling the polycrystalline silicon rods from the at least one reactor, comminuting the deinstalled polycrystalline silicon rods into chunks, wherein the deinstallation of the polycrystalline silicon rods from the at least one reactor is followed by, and the comminution of the deinstalled polycrystalline silicon rods into chunks is preceded by, classification of the polycrystalline silicon rods or rod form parts derived therefrom into at least two quality classes on the basis of the rod or rod part diameter and at least one additional feature, said at least two quality classes being sent to separate comminution steps, wherein the at least one additional feature is the position of silicon in the rod, the position of the rod in the reactor, a visually discernible feature, a measurable feature, or a combination thereof.

17. A process for producing polycrystalline silicon, comprising depositing polycrystalline silicon on support bodies present in at least one reactor to obtain polycrystalline silicon rods, deinstalling the polycrystalline silicon rods from the at least one reactor, comminuting the deinstalled polycrystalline silicon rods into chunks, wherein the deinstallation of the polycrystalline silicon rods from the at least one reactor is followed by, and the comminution of the deinstalled polycrystalline silicon rods into chunks is preceded by, classification of whole polycrystalline silicon rods, or rod form parts separated from one polycrystalline silicon rod, into at least two quality classes on the basis of the rod diameter and at least one additional feature, said at least two quality classes being sent to separate comminution steps, wherein the at least one additional feature is a feature selected from the group consisting of;
 position of the silicon in the rod,
 position of the rod in the reactor
 fracture characteristics of the rods or rod parts spontaneously or on fragmentation by
 mechanical, thermal, or electrical methods, refractive indices of the rods or rod parts for sound, infrasound, or ultrasound waves
 emission spectrum of the rods or rod parts after excitation including thermal, electrical, or optically excitations, or in an unexcited state
 electromagnetic absorption spectrum of the rods or rod parts
 neutron activatability of the rods or rod parts
 shape of the rods or rod parts
 length of the rods
 weight of the rods or rod parts
 porosity of the rods or rod parts
 density of the rods or rod parts
 contamination of the surface or of the volume selected from the group consisting of
 surface contamination of the rods or rod parts with metals, nonmetals or compositions thereof,
 contamination of the volume of the rods or rod parts with metals, nonmetals or compositions thereof,
 contamination of the surface of the rods or rod parts with dust
 air temperature, air composition and time up to classification
 state of the integrity and contamination of deposition reactor after deposition
 the interface of the filament rods with the deposited silicon including color, shape, thickness and composition of any existing intermediate layer, and bond strength
 contact of the rods or rod parts with extraneous materials
 the odor of the rods or rod parts
 sound of the rods or rod parts after mechanical excitation
 intrinsic vibration frequency of the rods or rod parts
 electrical resistance of the rods or rod parts refractive indices of the rods or rod parts for electromagnetic waves
X-ray diffraction characteristics of the rods or rod parts
X-ray absorption characteristics of the rods or rod parts
isotope composition of the rods or rod parts
reflectivity of the surface of the rods or rod parts for various wavelengths of electromagnetic radiation
reflectivity of fracture surfaces of the rods or rod parts for various wavelengths of electromagnetic radiation
impedance of the rods or rod parts for electromagnetic or sound waves of different frequencies
crystal structure of the rods or rod parts
the crystallite size, type, shape and arrangement in regions within or on the surface of rods or rod parts
the reaction characteristics of the rods or rod parts with various chemicals
hardness of the rods or rod parts
flexural strength of the rods or rod parts
tensile strength of the rods or rod parts
compressive strength of the rods or rod parts
shear strength of the rods or rod parts
stresses within the rods or rod parts
moment of inertia of the rods or rod parts
thermal conductivity of the rods or rod parts
electromagnetic permeability of the rods or rod parts
neutron diffraction characteristics of the rods or rod parts
neutron absorption characteristics of the rods or rod parts
nuclear spin resonance characteristics of the rods or rod parts
electrical capacitance of the rods or rod parts
electromagnetic inductivity of the rods or rod parts
magnetization of the rods or rod parts
magnetic moment of the rods or rod parts
magnetic susceptibility of the rods or rod parts
radioactivity of the rods or rod parts
heat transfer coefficient of the surface or fracture surface of the rods or rod parts
electrical polarizability of the rods or rod parts
electrical permittivity of the rods or rod parts
the particle emission of the rods or rod parts
color of the rods or rod parts
gloss of the rods or rod parts
stains on the surface of the rods or rod parts
surface deformations of the rods or rod parts
surface structure of the rods or rod parts
appearance of the rods or rod parts including personal visual quality impression
the presence or absence of gas-filled or unfilled cavities within the rods or rod parts and combinations thereof.

* * * * *